(12) United States Patent
Yuasa

(10) Patent No.: US 10,557,791 B2
(45) Date of Patent: Feb. 11, 2020

(54) OPTICAL ANALYZER

(71) Applicant: TOPCON CORPORATION, Itabashi-ku (JP)

(72) Inventor: Taichi Yuasa, Itabashi-ku (JP)

(73) Assignee: TOPCON CORPORATION, Tokyo (JP)

( * ) Notice: Subject to any disclaimer, the term of this patent is extended or adjusted under 35 U.S.C. 154(b) by 17 days.

(21) Appl. No.: 15/545,387

(22) PCT Filed: Jan. 19, 2016

(86) PCT No.: PCT/JP2016/051366
§ 371 (c)(1),
(2) Date: Jul. 21, 2017

(87) PCT Pub. No.: WO2016/117530
PCT Pub. Date: Jul. 28, 2016

(65) Prior Publication Data
US 2018/0003628 A1    Jan. 4, 2018

(30) Foreign Application Priority Data

Jan. 22, 2015  (JP) ................................ 2015-010131

(51) Int. Cl.
*G01N 33/38* (2006.01)
*G01N 21/359* (2014.01)
*G01N 21/3563* (2014.01)

(52) U.S. Cl.
CPC ....... *G01N 21/359* (2013.01); *G01N 21/3563* (2013.01); *G01N 33/383* (2013.01);
(Continued)

(58) Field of Classification Search
CPC ............. G01N 21/359; G01N 21/3563; G01N 33/383; G01N 2201/061;
(Continued)

(56) References Cited

U.S. PATENT DOCUMENTS

| | | |
|---|---|---|
| 6,219,476 B1 | 4/2001 | Kususawa et al. |
| 7,006,690 B1 | 2/2006 | Imura |

(Continued)

FOREIGN PATENT DOCUMENTS

| | | |
|---|---|---|
| JP | 61-102505 | 5/1986 |
| JP | 02-061540 | 3/1990 |

(Continued)

OTHER PUBLICATIONS

International Search Report dated Apr. 5, 2016 in PCT/JP2016/051366 filed Jan. 19, 2016.
(Continued)

*Primary Examiner* — Collin X Beatty
(74) *Attorney, Agent, or Firm* — Xsensus LLP

(57) ABSTRACT

A spectroscopic measuring device includes a halogen lamp as a light source, a lens of an irradiating system, a mirror, and a spectrometer. The lens of the irradiating optical system emits light from the halogen lamp to a measurement object. The mirror is an optical member, and the mirror is arranged coaxial with the lens and conducts detecting light between the halogen lamp and the measurement object, to the spectrometer. The spectrometer is an analyzing part and analyzes material of the measurement object on the basis of the light received via the mirror. The light from the halogen lamp to the measurement object passes through the peripheral part of the optical axis of the lens, and the light to be received by the spectrometer passes through the center part of the optical axis of the lens, at the position of the mirror.

6 Claims, 2 Drawing Sheets

(52) U.S. Cl.
CPC . *G01N 2201/061* (2013.01); *G01N 2201/068* (2013.01); *G01N 2201/0637* (2013.01)

(58) Field of Classification Search
CPC ...... G01N 2201/0637; G01N 2201/068; G01J 3/0208; G01J 3/021; G01J 3/0216; G01J 3/10; G01J 3/2823
USPC .................................................. 359/850, 618
See application file for complete search history.

(56) References Cited

U.S. PATENT DOCUMENTS

| | | | | |
|---|---|---|---|---|
| 7,130,033 | B2* | 10/2006 | Delacour | G01N 21/55 356/121 |
| 2007/0153368 | A1* | 7/2007 | Vucinic | G01N 21/6458 359/368 |
| 2010/0096554 | A1* | 4/2010 | Shirota | G01N 21/94 250/341.8 |
| 2013/0021602 | A1* | 1/2013 | Dribinski | G02F 1/37 356/237.3 |
| 2014/0104618 | A1* | 4/2014 | Potsaid | G02B 26/105 356/497 |
| 2014/0268127 | A1* | 9/2014 | Day | G01J 3/0291 356/300 |
| 2016/0356644 | A1* | 12/2016 | Hodgkiss | G01N 21/6408 |

FOREIGN PATENT DOCUMENTS

| | | |
|---|---|---|
| JP | H04299207 A | 10/1992 |
| JP | 2000-111832 | 4/2000 |
| JP | 2001099711 A | 4/2001 |
| JP | 2008-14779 A | 1/2008 |
| JP | 2014-149286 A | 8/2014 |
| WO | 2014118935 A1 | 7/2014 |

OTHER PUBLICATIONS

Japanese Office Action dated Jan. 7, 2019, issued in Japanese Patent No. 2015-010131, along with a machine-generated English translation.
Japanese Notification of Reasons for Refusal dated Sep. 4, 2018 in Japanese Application No. 2015-010131.
Japanese Office Action dated Jun. 26, 2019, issued in corresponding Japanese Patent Application No. 2015-010131.

* cited by examiner

OPTICAL ANALYZER

TECHNICAL FIELD

The present invention relates to an optical analyzer for spectroscopic measurement.

BACKGROUND ART

Deterioration and damage to concrete can be diagnosed by analyzing light that has been reflected from the concrete after near infrared light is emitted onto the concrete. One such technique is disclosed in, for example, Japanese Unexamined Patent Application Laid-Open No. 2000-14779. This technique can be applied to buildings and structures that are made of concrete, such as a tunnel having an inner wall, a bridge having a concrete portion, and one having a concrete wall.

This technique uses a light source that satisfies the following requirements.
(1) Near infrared light having a wavelength of approximately 0.9 to 2.5 µm can be emitted.
(2) Light amount necessary to diagnose even when a distance from the light source to a measurement point is approximately 10 meters, can be obtained.
(3) Characteristics are stable to temperature variation and other external factors because the light source is basically used outdoors.

The light source that satisfies these requirements may be a halogen lamp or a halogen heater.

Moreover, a simply constructed optical system using no special components is necessary in view of outdoor use and cost. Furthermore, this technique involves spectroscopic measurement to conduct diagnosis, and therefore, high wavelength resolution is required to increase the precision of the diagnosis.

DISCLOSURE OF THE INVENTION

In view of these circumstances, an object of the present invention is to provide an optical analyzer having a simple optical system and having high wavelength resolution.

A first aspect of the present invention provides an optical analyzer including a light source, an irradiating optical system, an optical member, and an analyzing part. The irradiating optical system emits light from the light source to a measurement object. The optical member shares an optical axis with the irradiating optical system and conducts the light between the light source and the measurement object, to a light receiving part. The analyzing part has the light receiving part, which receives the light via the optical member, and analyzes the material of the measurement object on the basis of the received light. The light from the light source to the measurement object passes through a peripheral part of the optical axis, and the light to be received by the light receiving part passes through a center part of the optical axis, at the position of the optical member.

A second aspect of the present invention provides an optical analyzer including an irradiating optical system, an analyzing part, and a reflector. The irradiating optical system has a light source, an elliptical mirror that concentrates light from the light source and that forms a secondary light source point, and a lens member that emits the light from the secondary light source point to a measurement object. The analyzing part receives at least some of the light that has been reflected from the measurement object and analyzes the material of the measurement object on the basis of the received light. The reflector is arranged so as to be coaxial with the irradiating optical system and conducts at least some of the light that has been reflected from the measurement object, to the analyzing part. The light to be reflected by the reflector after being reflected from the measurement object has a light flux diameter smaller than that of the light emitted from the irradiating optical system.

A third aspect of the present invention provides an optical analyzer including an irradiating optical system and an analyzing part. The irradiating optical system has a light source, an elliptical mirror that concentrates light from the light source and that forms a secondary light source point, a lens member that shapes the light from the secondary light source point into a beam as irradiating light, and a reflector that reflects the irradiating light from the lens member to a measurement object. The analyzing part receives at least some of the light that has been reflected from the measurement object and analyzes the material of the measurement object on the basis of the received light. A center part of the reflector is made so that the light that has been reflected from the measurement object passes therethrough. The light that has passed through the center part of the reflector after being reflected from the measurement object, is received by the analyzing part.

According to a fourth aspect of the present invention, in the invention according to any one of the first to the third aspects of the present invention, the light source may use a filament to emit light.

According to a fifth aspect of the present invention, in the invention according to any one of the first to the fourth aspects of the present invention, the light source may be a halogen lamp or a halogen heater, which emits light having a wavelength of 0.9 to 2.5 µm.

Effects of the Invention

The present invention provides an optical analyzer having a simple optical system and having high wavelength resolution.

Figure 1:
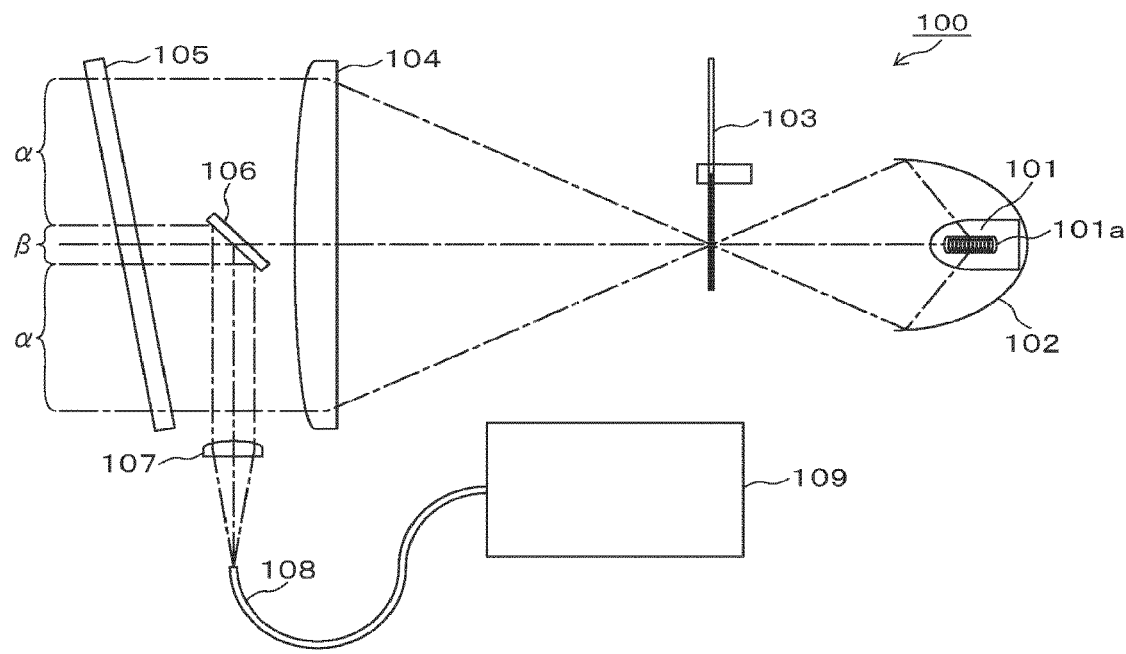
FIG. 1 is a conceptual diagram of an embodiment of the present invention.

EXPLANATION OF REFERENCE NUMERALS 100 denotes a spectroscopic measuring device, 101 denotes a halogen lamp (halogen heater), 101a denotes a filament, 102 denotes an elliptical mirror, 103 denotes an optical chopper, 104 denotes a lens of an irradiating system, 105 denotes a window glass, 106 denotes a mirror, 107 denotes a lens of a light receiving system, 108 denotes an optical fiber, 109 denotes a spectrometer, 200 denotes a spectroscopic measuring device, 300 denotes a spectroscopic measuring device, and 301 denotes a mirror.

DETAILED DESCRIPTION OF PREFERRED EMBODIMENTS

FIG. 1 shows a spectroscopic measuring device 100 as an embodiment of the optical analyzer of the present invention.

The spectroscopic measuring device 100 includes a halogen lamp 101, an elliptical mirror 102, an optical chopper 103, a lens 104 of an irradiating system, a window glass 105, a mirror 106, a lens 107 of a light receiving system, a light receiving fiber 108, and a spectrometer 109.

The halogen lamp 101 emits light in a bandwidth including near infrared light with a wavelength of approximately 0.9 to 2.5 µm while the filament 101a is energized. Although a case of using the halogen lamp as the light source is exemplified here, a halogen heater may be used as the light source. A halogen heater is commonly used for providing radiant heat, which is generated from its filament while the filament is energized. However, near infrared light having a wavelength of 0.9 to 2.5 µm is also obtained when the radiant heat is emitted, and therefore, the halogen heater can be used as the light source of the present invention.

The elliptical mirror 102 concentrates the light from the halogen lamp 101 at the position of the optical chopper 103, which is positioned at a secondary light source. The optical chopper 103 chops the light from the halogen lamp 101 to a measurement point, at a predetermined frequency. The light that is emitted to the measurement point becomes intermittent light having the predetermined frequency after passing through the optical chopper 103.

In this embodiment, the optical chopper 103 is located at the position of the secondary light source, which is after a first light source using the halogen lamp 101. The secondary light source has a light flux diameter of approximately 10 mm and generates a blurred point image at the position of the optical chopper 103. The reason for this is as follows. Basically, the filament 101a has a three-dimensional shape and is not a point light source, and thus, the light emitted from the filament 101a contains a large number of components other than parallel light. Such light emitted from the filament 101a generates a blurred point image, which tends to be approximately 10 mm in diameter, at the secondary light source position because the light is not condensed at a point even when concentrated by the elliptical mirror.

The lens 104 of the irradiating system shapes the emitted light, which has been chopped by the optical chopper 103, into a beam of irradiating light to the measurement point. The diameter of the lens 104 of the irradiating system is, for example, approximately 125 mm. The lens 104 of the irradiating system is a high NA lens, which has a long focal distance and a large effective diameter relative to the lens 107 of the light receiving system. The lens 104 of the irradiating system is set so that its focal point will be located 2 to 10 meters ahead. As described later, the focal point of the optical system of the irradiating system may not necessarily be positioned with high precision because light is emitted from the light source formed of the filament 101a in the spectroscopic measuring device 100. That is, the focal point of the optical system of the irradiating system can be positioned at a position of approximately the maximum assumed measurement distance. Naturally, the lens 104 of the irradiating system may be configured to be movable in accordance with the distance to the measurement point.

The window glass 105 protects the optical systems from external influences. The window glass 105 is made of a material that has high transmittance with respect to near infrared light having a wavelength of approximately 0.9 to 2.5 µm, which is to be generated from the halogen lamp 101.

The mirror 106 is a plane mirror and reflects the irradiating light that has been reflected from the measurement point, which is hereinafter called "detecting light", to the lens 107 of the light receiving system. The mirror 106 reflects the detecting light from the measurement point in a direction 90 degrees relative to the optical axis of the lens 104 of the irradiating system. The mirror 106 is arranged at the position of the center of the optical axis of the lens 104 of the irradiating system and is coaxial with the lens 104 of the irradiating system. That is, the mirror 106 reflects the detecting light, which has returned from the measurement point on the same optical axis as the irradiating light to the measurement point, in the direction 90 degrees relative to the optical axis to the lens 107 of the light receiving system. The apparent area of the mirror 106 as seen from the measurement point is approximately 1.5% of the area of the lens 104 of the irradiating system.

The mirror 106 has a first optical axis that connects the measurement point and the center of the mirror 106 and has a second optical axis that corresponds to the optical axis of the lens 107 of the light receiving system. The coaxial structure described above shows that the first optical axis of the mirror 106 is coaxial with the optical axis of the lens 104 of the irradiating system. The lens 107 of the light receiving system is a low NA lens, which has a short focal distance and a small effective diameter relative to the lens 104 of the irradiating system, and the lens 107 conducts the detecting light, which has been reflected by the mirror 106, to the light receiving fiber 108. The lens 107 of the light receiving system and the light receiving fiber 108 are arranged so that the incident position at the light receiving fiber 108 will be located at the position of the focal point of the lens 107 of the light receiving system.

The light receiving fiber 108 is an optical fiber and has a fiber diameter of, for example, approximately 0.6 mm or less. The spectrometer 109 performs spectroscopic analysis on the detecting light that is input via the light receiving fiber 108 and obtains information relating to the material of the measurement point. The spectrometer 109 may be of a type that disperses the detecting light into a spectrum by using a diffraction grating, a prism, or a linear variable filter (LVF) or may be a type that generates multiple lights in multiple wavebands by using optical filters. The spectrometer 109 uses an optical detection element, which may be a detection element of each kind, such as an avalanche photodiode (APD) or a line sensor.

The processing of the spectrometer 109 is performed by a publicly known method, such as one disclosed in Japanese Unexamined Patent Application Laid-Open No. 2000-14779. The following briefly describes the principle of the basic processing to be performed by the spectrometer 109. First, near infrared light having a predetermined spectrum is emitted to a reference sample of which the composition or the material is known, and then spectral information of the detecting light is obtained in advance. The spectral information is digital data and is stored in a memory within the spectrometer 109. In actual measurement, spectral information that is obtained from detecting light and the spectral information that is obtained in advance are compared with each other, whereby the condition of the measurement point is evaluated.

The lens 107 is small in size relative to the lens 104 of the irradiating system in the spectroscopic measuring device 100 for the reason described below. Essentially, lower NA is preferable in the lens 107 of the light receiving system to obtain high wavelength resolution. This is because the influence of the aberration of the lens 107 of the light receiving system increases to an unacceptable degree when the NA is high. On the other hand, the device may be increased in size when the lens 107 of the light receiving system has a long focal distance, and therefore, the lens 107 of the light receiving system is desired to have a short focal distance. Additionally, the amount of light to be received scarcely increases even by increasing the diameter of the lens when the NA of the lens 107 of the light receiving system is constant.

Thus, the lens 107 of the light receiving system can be designed to be small, whereby the area of the mirror 106 can be set to be small because the size of the mirror 106 corresponds to the diameter of the lens 107 of the light receiving system.

Meanwhile, the lens 104 of the irradiating system has high NA and a large diameter relative to the lens 107 of the light receiving system, to increase the light flux that is taken from the light source. Additionally, the lens 104 of the irradiating system has a long focal point because a smaller light flux diameter at a long distance increases the efficiency of receiving light from the long distance by which the amount of the received light tends to be small. Consequently, the mirror 106 is made small relative to the lens 104 of the irradiating system and is arranged coaxial with the lens 104 of the irradiating system. In this structure, the irradiating light and the detecting light to be reflected by the mirror 106 share the optical axis, and the irradiating light passes through the peripheral part of the optical axis of the lens 104 of the irradiating system while the detecting light to be reflected by the mirror 106 passes through the center part of the optical axis.

As described above, the spectroscopic measuring device 100 includes the halogen lamp 101 as a light source, the lens 104 of the irradiating system, the mirror 106, and the spectrometer 109. The lens 104 constitutes the irradiating optical system that emits light from the halogen lamp 101 to a measurement object. The mirror 106 is an optical member, and the mirror 106 is arranged coaxial with the lens 104 of the irradiating system and conducts the detecting light between the halogen lamp 101 and the measurement object, to the spectrometer 109. The spectrometer 109 is an analyzing part and analyzes the material of the measurement object on the basis of the light received via the mirror 106. The light from the halogen lamp 101 to the measurement object passes through the peripheral part α of the optical axis of the lens 104 of the irradiating system, and the light to be received by the spectrometer 109 passes through the center part β of the optical axis of the lens 104 of the irradiating system, at the position of the mirror 106.

In another aspect, the spectroscopic measuring device 100 includes the irradiating optical system, the spectrometer 109, and the mirror 106. The irradiating optical system has the halogen lamp 101 as a light source, the elliptical mirror 102 that concentrates the light from the light source and that forms a secondary light source point, and the lens 104 that is a lens member and that emits the light from the secondary light source point to a measurement object. The spectrometer 109 is an analyzing part, and the spectrometer 109 receives at least some of the light that has been reflected from the measurement object and analyzes the material of the measurement object on the basis of the received light. The mirror 106 is arranged coaxial with the irradiating optical system and conducts at least some of the light that has been reflected from the measurement object, to the spectrometer 109. The light that has been reflected by the mirror 106 after being reflected from the measurement object has a light flux diameter smaller than that of the light emitted from the irradiating optical system containing the lens 104.

Operation

The light from the halogen lamp 101 is reflected by the elliptical mirror 102 and is concentrated at the position of the optical chopper 103. This light is chopped by the optical chopper 103 and is made into a light flux by the lens 104 of the irradiating system so as to be condensed to the measurement point, and the light flux is emitted to the measurement point. The light that has been reflected from the measurement point is reflected by the mirror 106 and is conducted to the light receiving fiber 108 as detecting light via the lens 107 of the light receiving system. The detecting light that has been conducted to the light receiving fiber 108 is further conducted to the spectrometer 109, at which the detecting light is subjected to spectroscopic analysis, whereby the composition or the material of the measurement point is analyzed and is evaluated. The analysis and the evaluation are used to diagnose, for example, the deterioration condition of a concrete wall surface.

For example, when concrete is deteriorated due to deterioration of the material, such as change in the composition and embrittlement, this deterioration can be detected by examining the spectral information of the detecting light.

Advantages

As described above, the irradiating light at the position of the focal point of the lens 104 of the irradiating system generates a blurred point image having a size of some degree because the light originates from the filament 101a. This tendency occurs in front of and at the back of the focal point of the lens 104 of the irradiating system. That is, the focal point of the irradiating light does not make a clear point image at the position of the focal point of the lens 104 of the irradiating system, but the condition of the image does not greatly vary in front of and at the back of the focal point on the optical axis. In other words, the focal point of the irradiating light is not clear, and the irradiating light generates a vague image, in a range of some extent on the optical axis.

Thus, the focal point of the lens 104 of the irradiating system can be set at an approximate position, and the position of the focal point does not greatly affect the measurement because the amount of light to be received scarcely varies even when the distance to the measurement point is slightly changed. Accordingly, the spectroscopic measurement is performed without any problem in practical use, even by using the fixed focal point. The fixed focal point enables simplification of the optical system.

The coaxial arrangement of the mirror 106 and the lens 104 of the irradiating system contributes to the simplified and small-sized optical system. Moreover, the size relationship, in which the diameter of the lens 104 of the irradiating system is larger than that of the lens 107 of the light receiving system, contributes to the small-sized mirror 106, thereby reducing shading of the irradiating light due to the mirror 106. Here, the "shading" is a phenomenon in which the light emitted from the lens 104 of the irradiating system to the measurement point is shaded by the mirror 106, whereby the light reflected from the measurement point is not suitably detected.

As described above, this embodiment uses the filament 101a to emit light, which contains a large number of components other than parallel light. This light is also reflected from a portion of the measurement target, which is shaded by the mirror 106 as seen from the lens 104 of the irradiating system in the case of using parallel light, and thus, the shading hardly occurs even when the distance to the measurement point is close, for example, several tens of centimeters.

The optical system shown in FIG. 1 has a simple structure with a small number of parts and is decreased in size as well as provides high wavelength resolution.

Modifications

Figure 2:
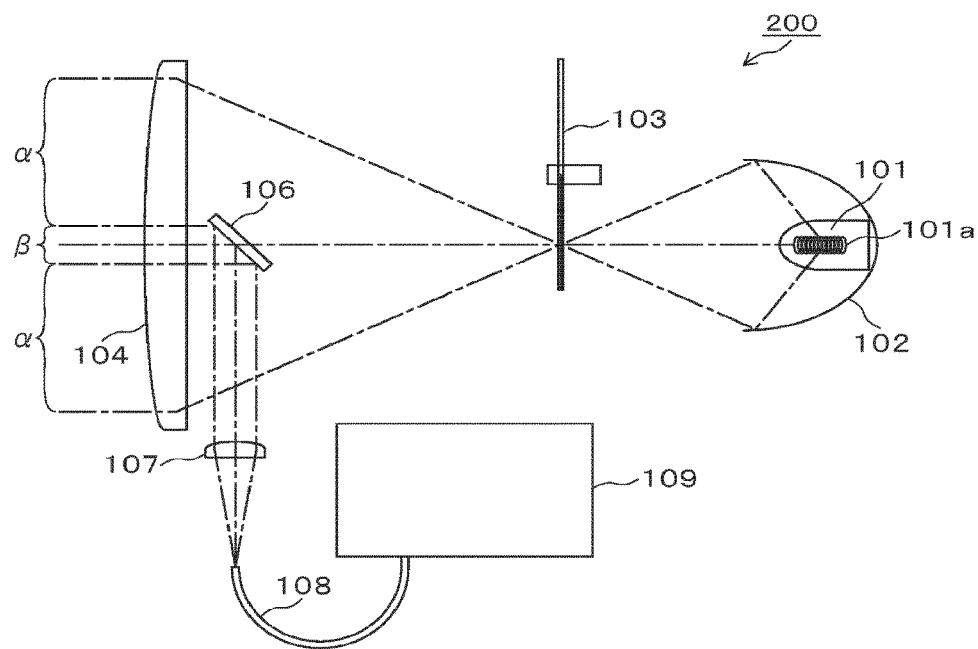
FIG. 2 is a conceptual diagram of another embodiment of the present invention.

FIG. 2 shows a spectroscopic measuring device 200 having an optical system that differs from the optical system shown in FIG. 1. The spectroscopic measuring device 200 has the mirror 106 that is arranged at the light source side of the lens 104 of the irradiating system and does not have the window glass 105, which is shown in FIG. 1. The other components are the same as those of the spectroscopic measuring device 100 in FIG. 1.

Figure 3:
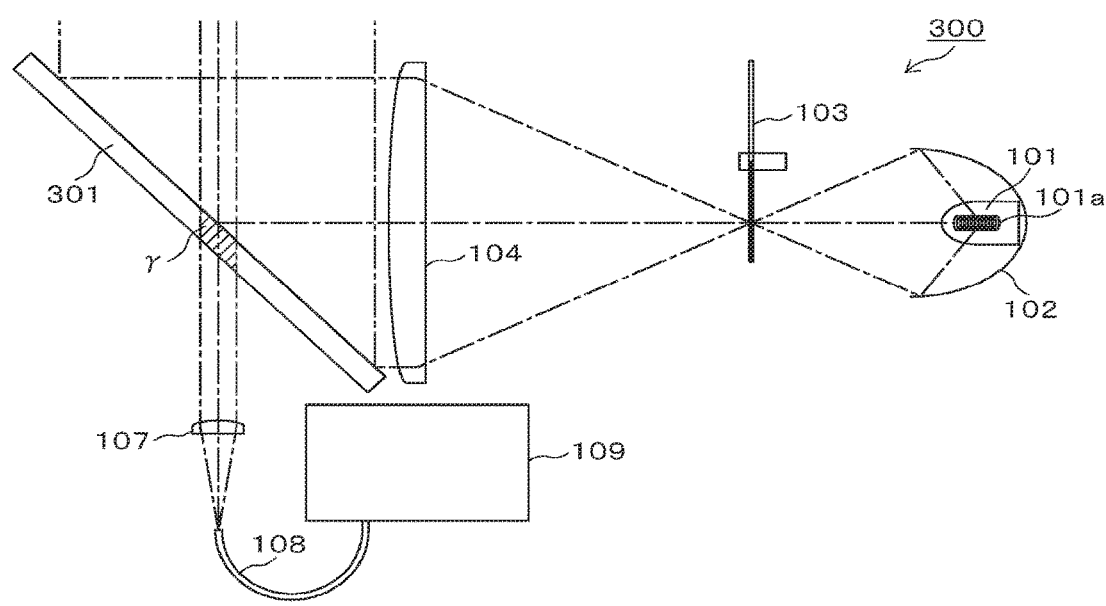
FIG. 3 is a conceptual diagram of yet another embodiment of the present invention, which differs from the embodiment shown in FIG. 2.

FIG. 3 shows a spectroscopic measuring device 300 that includes an irradiating optical system and the spectrometer 109. The irradiating optical system has the halogen lamp 101 as a light source, the elliptical mirror 102, the lens 104, and a mirror 301. The elliptical mirror 102 concentrates light from the halogen lamp 101 and forms a secondary light source point. The lens 104 shapes the light from the secondary light source point into a beam as irradiating light. The mirror 301 is a reflector and reflects the irradiating light from the lens 104 to a measurement object. The spectrometer 109 is an analyzing part, and the spectrometer 109 receives at least some of the light that has been reflected from the measurement object and analyzes the material of the measurement object on the basis of the received light. The spectroscopic measuring device 300 is configured such that all or some of the light that has been reflected from the measurement object passes through the center part of the mirror 301 and is then received by the spectrometer 109.

In the spectroscopic measuring device 300, light is emitted from the halogen lamp 101 of the light source and passes through the lens 104 of the irradiating system, and then the light is reflected by the mirror 301 and is emitted to the measurement object. The mirror 301 has a center part made of a material that transmits near infrared light or has a hole at the center part, so that detecting light, that is, near infrared light to be detected, will pass therethrough. The center part is indicated by the symbol "γ". The light that has been reflected from the measurement object passes through the center part γ and reaches the lens 107 of the light receiving system.

The optical axis of the optical system of the irradiating system and the optical axis of the optical system of the light receiving system may not necessarily perfectly coincide with each other and may be slightly shifted from each other. Light having a wavelength of less than 0.9 μm or greater than 2.5 μm may also be used. Additionally, a light source having a relatively large emission area may also be used instead of the light source using the filament. The material of the measurement object is not limited to concrete and may be lumber, plants, food, ceramics, metal, each kind of construction material, and other material that may deteriorate.

The invention claimed is:

1. An optical analyzer comprising:
    an irradiating optical system having a light source, an elliptical mirror that concentrates light from the light source and that forms a secondary light source point, and a lens member that condenses the light from the secondary light source point to a measurement point of a measurement object as irradiating light;
    a spectrometer that receives at least some of the light that has been reflected from the measurement object and that analyzes the material of the measurement object on the basis of the received light; and
    a reflector that is arranged so as to be coaxial with the irradiating optical system and to be in light flux of the irradiating light, the reflector configured to reflect at least some of the light that has been reflected back from the measurement object to the lens member by returning on an optical axis of the irradiating optical system while passing through a path that is passed through by the irradiating light, and the reflector configured to reflect the at least some of the light in a direction different from the direction of the optical axis of the irradiating optical system between the lens member and the light source or between the lens member and the measurement object, thereby conducting the at least some of the light to the spectrometer,
    wherein the at least some of the light to be reflected by the reflector after being reflected back from the measurement object has a light flux diameter at a position of the reflector, and the light flux diameter is smaller than a light flux diameter, at the position of the reflector, of the irradiating light that is emitted from the lens member to the measurement object.

2. The optical analyzer according to claim 1, wherein the light source emits light by using a filament.

3. The optical analyzer according to claim 1, wherein the light source is a halogen lamp or a halogen heater, which emits light having a wavelength of 0.9 to 2.5 μm.

4. An optical analyzer comprising:
    an irradiating optical system having a light source, an elliptical mirror that concentrates light from the light source and that forms a secondary light source point, a lens member that shapes the light from the secondary light source point into a beam as irradiating light, and a reflector that reflects the irradiating light from the lens member to a measurement object; and
    a spectrometer that receives at least some of the light that has been reflected from the measurement object and that analyzes the material of the measurement object on the basis of the received light,
    wherein a center part of the reflector is made so that the light that has been reflected from the measurement object passes therethrough, and the light that has passed through the center part of the reflector after being reflected from the measurement object, is received by the spectrometer.

5. The optical analyzer according to claim 4, wherein the light source emits light by using a filament.

6. The optical analyzer according to claim 4, wherein the light source is a halogen lamp or a halogen heater, which emits light having a wavelength of 0.9 to 2.5 μm.

* * * * *